(12) United States Patent
Minai et al.

(10) Patent No.: US 8,480,564 B2
(45) Date of Patent: Jul. 9, 2013

(54) CAPSULE TYPE MEDICAL APPARATUS AND CAPSULE TYPE MEDICAL SYSTEM

(75) Inventors: Tetsuo Minai, Hachioji (JP); Kazuaki Tamura, Hachioji (JP); Jin Ohara, Hachioji (JP)

(73) Assignee: Olympus Corporation, Tokyo (JP)

( * ) Notice: Subject to any disclaimer, the term of this patent is extended or adjusted under 35 U.S.C. 154(b) by 233 days.

(21) Appl. No.: 12/751,020

(22) Filed: Mar. 31, 2010

(65) Prior Publication Data

US 2010/0191055 A1    Jul. 29, 2010

Related U.S. Application Data

(63) Continuation of application No. PCT/JP2008/066337, filed on Sep. 10, 2008.

(30) Foreign Application Priority Data

Oct. 1, 2007  (JP) ................. 2007-257950
Feb. 13, 2008  (JP) ................. 2008-032134

(51) Int. Cl.
*A61B 1/04*    (2006.01)
*A61B 1/06*    (2006.01)

(52) U.S. Cl.
USPC .......................................... 600/109; 600/160

(58) Field of Classification Search
USPC ................... 600/109, 117, 118, 121, 160
See application file for complete search history.

(56) References Cited

U.S. PATENT DOCUMENTS

| | | | |
|---|---|---|---|
| 6,115,636 A * | 9/2000 | Ryan ......................... | 607/60 |
| 7,914,442 B1 * | 3/2011 | Gazdzinski ................. | 600/109 |
| 2004/0225223 A1 * | 11/2004 | Honda et al. .............. | 600/476 |
| 2005/0027330 A1 | 2/2005 | Govari | |
| 2006/0243288 A1 | 11/2006 | Kim et al. | |
| 2007/0055098 A1 | 3/2007 | Shimizu et al. | |
| 2007/0149086 A1 * | 6/2007 | Nakamura ................. | 445/23 |
| 2009/0304093 A1 * | 12/2009 | Shim et al. ............... | 375/259 |

FOREIGN PATENT DOCUMENTS

| | | |
|---|---|---|
| EP | 1 502 540 A1 | 2/2005 |
| JP | 2005-87726 | 4/2005 |
| JP | 2006-051336 | 2/2006 |
| JP | 2006-513670 | 4/2006 |

(Continued)

OTHER PUBLICATIONS

English Abstract only of WO 2005/082229.

(Continued)

*Primary Examiner* — Philip R Smith
*Assistant Examiner* — William Chou
(74) *Attorney, Agent, or Firm* — Scully, Scott, Murphy & Presser, P.C.

(57) ABSTRACT

The present invention provides a capsule type medical apparatus that can receive, in a subject, an external signal transmitted from an outside of the subject and transmitted via a conductor existing in the subject, including: a cover member that is formed of a dielectric and covers components of the capsule type medical apparatus; a plurality of electrodes that are formed of conductors, are provided in tight contact with an inner wall side of the cover member, and receive the external signal; an inductor circuit that is connected in series to each of the plurality of electrodes, and has an inductance value set to configure a resonant circuit having a frequency substantially equal to a carrier frequency of the external signal as a resonant frequency; and a signal receiving circuit to which the external signal received by the plurality of electrodes and a potential difference of the external signal are inputted.

5 Claims, 10 Drawing Sheets

FOREIGN PATENT DOCUMENTS

| | | |
|---|---|---|
| JP | 2007-068622 | 3/2007 |
| KR | 10-2005-0099546 A | 10/2005 |
| KR | 10-2005-0121059 A | 12/2005 |
| KR | 10-2006-0002449 A | 1/2006 |
| KR | 10-2006-0013520 A | 2/2006 |
| KR | 10-2007-0018858 A | 2/2007 |
| WO | WO 2004/068748 A1 | 8/2004 |
| WO | WO 2004/091361 A2 | 10/2004 |
| WO | WO 2007/029453 A1 | 3/2007 |

OTHER PUBLICATIONS

International Search Report dated Dec. 9, 2008.
Extended Supplementary European Search Report dated Oct. 19, 2010.

\* cited by examiner

US 8,480,564 B2

CAPSULE TYPE MEDICAL APPARATUS AND CAPSULE TYPE MEDICAL SYSTEM

CROSS REFERENCE TO RELATED APPLICATION

This application is a continuation application of PCT/JP2008/066337 filed on Sep. 10, 2008 and claims benefit of Japanese Applications No. 2007-257950 filed in Japan on Oct. 1, 2007, and No. 2008-032134 filed in Japan on Feb. 13, 2008, the entire contents of which are incorporated herein by their reference.

BACKGROUND OF THE INVENTION

1. Field of the Invention

The present invention relates to a capsule type medical apparatus and a capsule type medical system, and more particularly to a capsule type medical apparatus and a capsule type medical system that receive information from an outside of a subject using the subject as a transmission medium.

2. Description of the Related Art

Endoscopes are conventionally widely used in a medical field or the like. Particularly, endoscopes in the medical field are mainly used for observing an inside of a living body. As one type of the above-described endoscope, a capsule type endoscope has been recently proposed that is swallowed by a human subject and placed in a body cavity, moves in the body cavity with peristaltic movement to successively pick up images of an object, and can transmit the picked-up images of the object to an outside as image pickup signals.

A device having substantially the same function as the above-described capsule type endoscope has been proposed, for example, in Japanese Patent Application Laid-Open Publication No. 2006-51336.

Japanese Patent Application Laid-Open Publication No. 2006-51336 discloses a capsule type endoscope that includes an antenna that can be used both for transmitting and receiving various signals by radio and a receiver unit, as a receiving system for receiving external signals from an external device, and can start, stop or change an operation mode of the endoscope itself based on contents of the external signals.

SUMMARY OF THE INVENTION

The present invention provides a capsule type medical apparatus that can receive, in a subject, an external signal transmitted from an outside of the subject and transmitted via a conductor existing in the subject, including: a cover member that is formed of a dielectric and covers components of the capsule type medical apparatus; a plurality of electrodes that are formed of conductors, are provided in tight contact with an inner wall side surface of the cover member, and receive the external signal; an inductor circuit that is connected in series to each of the plurality of electrodes, and has an inductance value set to configure a resonant circuit having a frequency substantially equal to a carrier frequency of the external signal as a resonant frequency; and a signal receiving circuit to which the external signal received by the plurality of electrodes and a potential difference of the external signal are inputted.

The present invention provides a capsule type medical system including: an external device that is provided outside a subject and can use a conductor existing in the subject as a transmission medium to transmit an external signal to an inside of the subject; and a capsule type medical apparatus that can receive the external signal in the subject, wherein the capsule type medical apparatus includes: a cover member that is formed of a dielectric and covers components of the capsule type medical apparatus; a plurality of electrodes that are formed of conductors, are provided in tight contact with a inner wall side surface of the cover member, and receive the external signal; an inductor circuit that is connected in series to each of the plurality of electrodes, and has an inductance value set to configure a resonant circuit having a frequency substantially equal to a carrier frequency of the external signal as a resonant frequency; and a signal receiving circuit to which the external signal received by the plurality of electrodes and a potential difference of the external signal are inputted.

DESCRIPTION OF THE PREFERRED EMBODIMENT(S)

Now, an embodiment of the present invention will be described with reference to the drawings.

Figure 1:
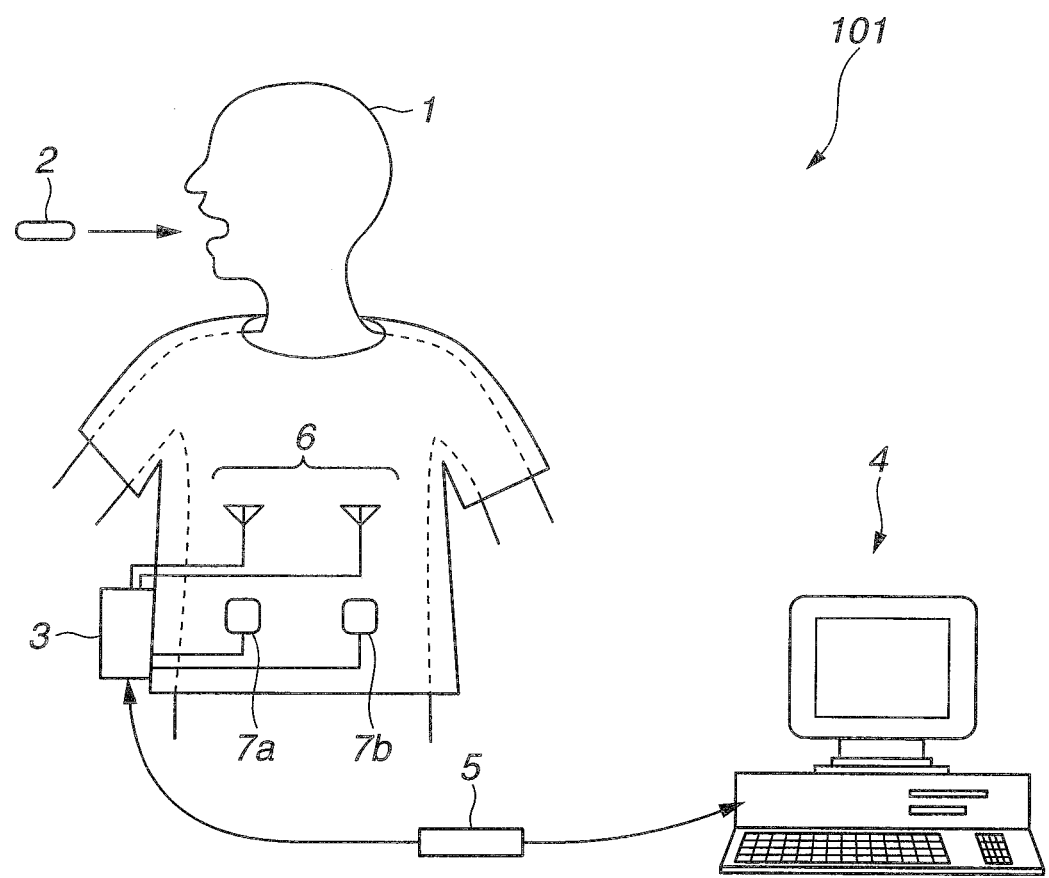
FIG. 1 is a view showing an example of a configuration of essential parts of a capsule type medical system that uses a capsule type medical apparatus of the present embodiment.
Figure 2:
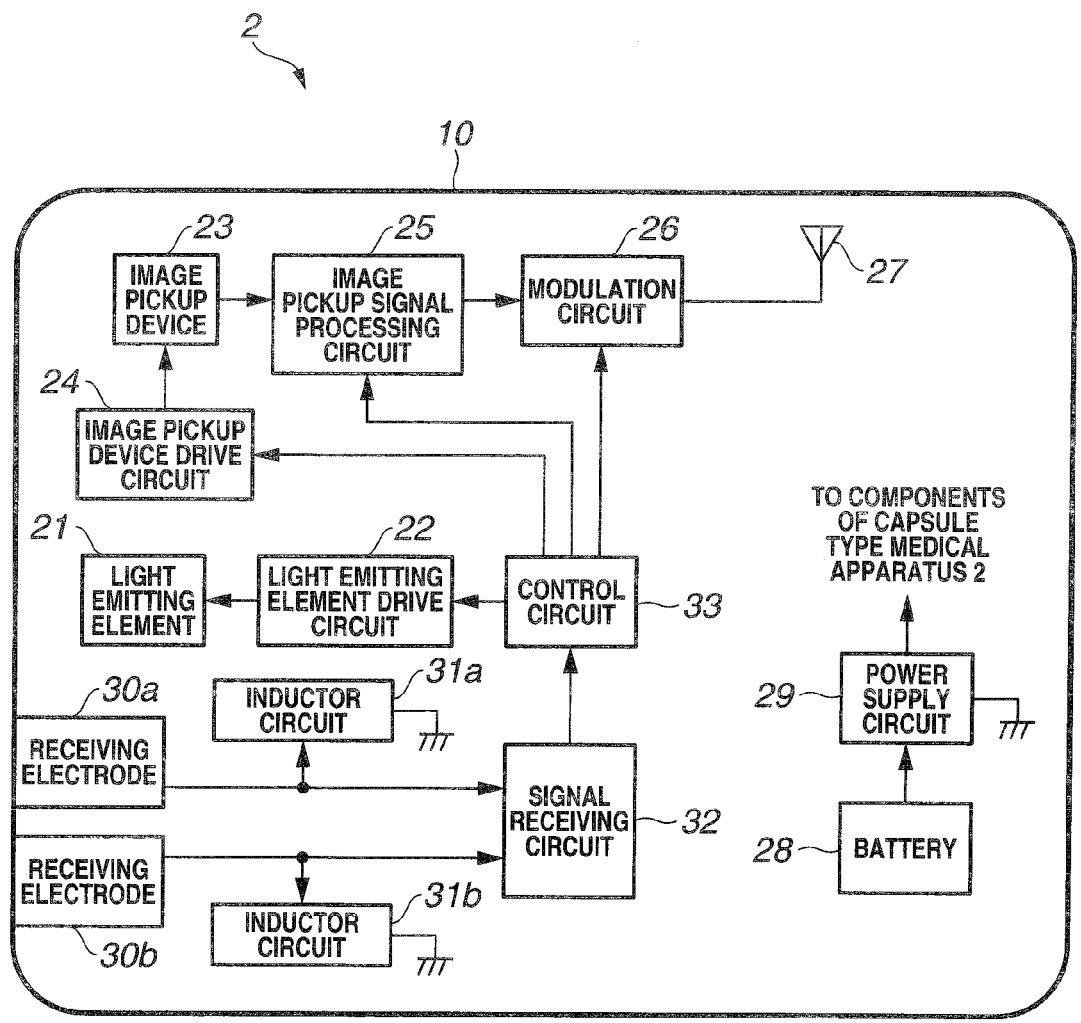
FIG. 2 is a block diagram showing an internal configuration of the capsule type medical apparatus in FIG. 1.
Figure 3:
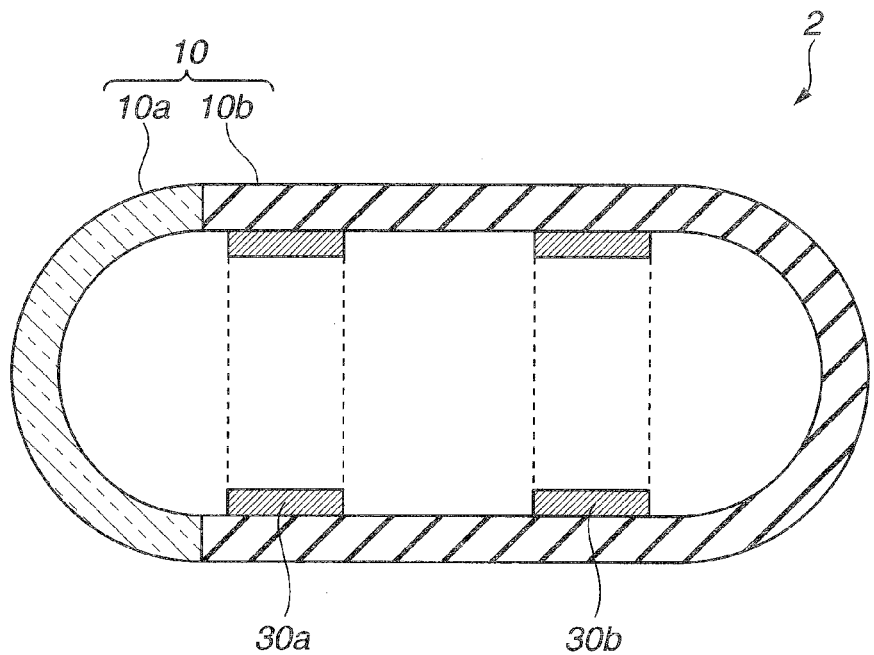
FIG. 3 is a schematic sectional view showing an arrangement state of receiving electrodes included in the capsule type medical apparatus in FIG. 1.
Figure 4:
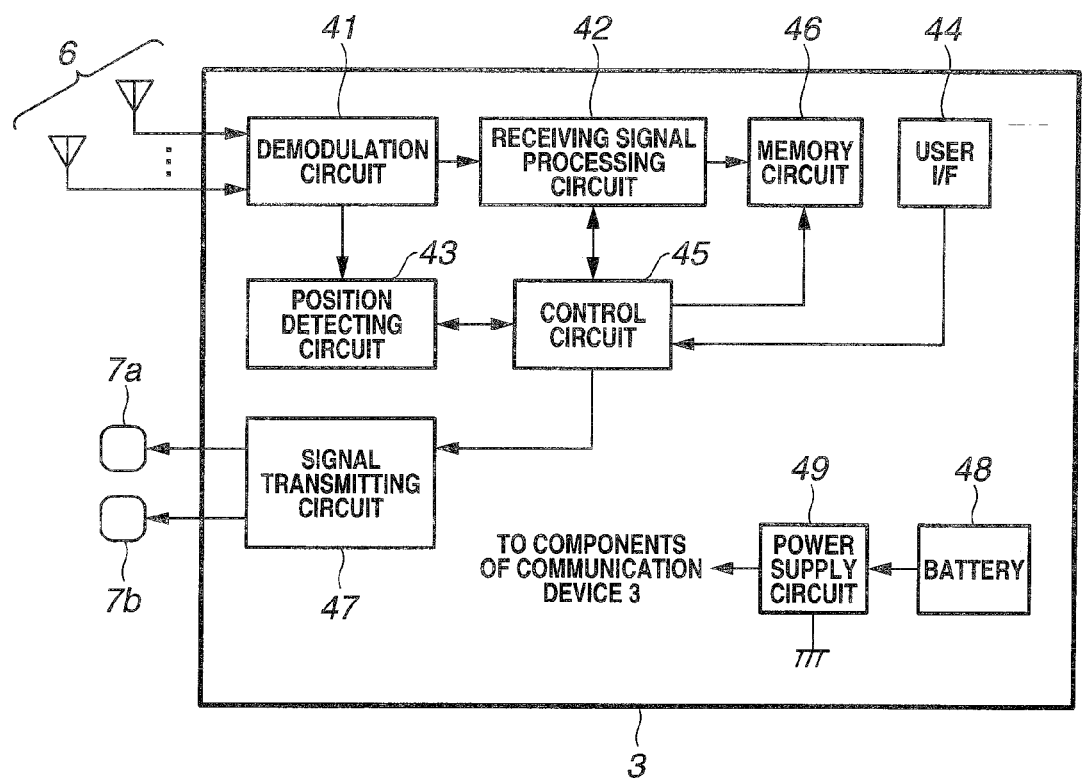
FIG. 4 is a block diagram of an internal configuration of a communication device in FIG. 1.
Figure 5:
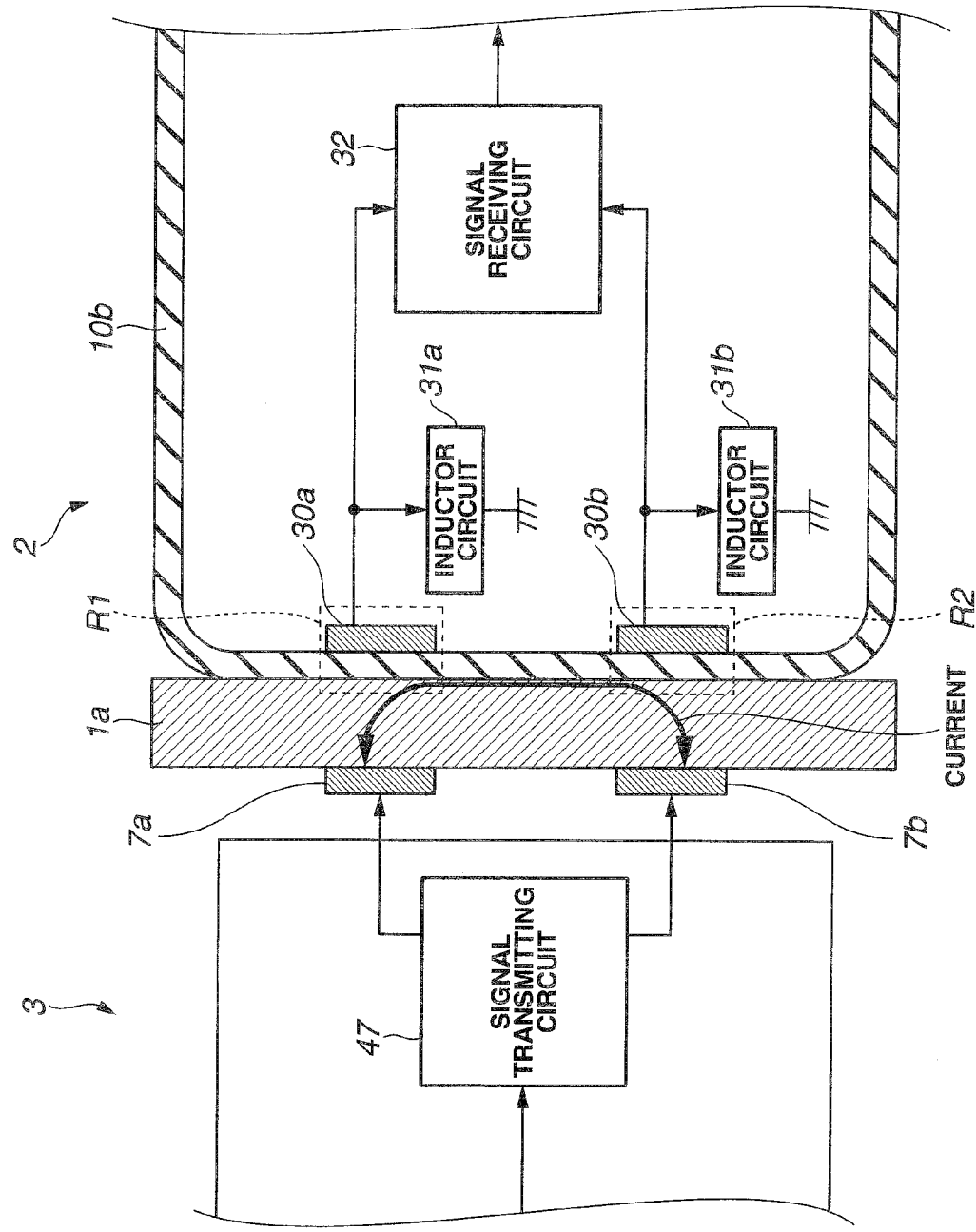
FIG. 5 is a schematic view showing a state where a signal is transmitted via a conductor existing in a subject.

FIGS. 1 to 5 relate to the embodiment of the present invention. FIG. 1 is a view showing an example of a configuration of essential parts of a capsule type medical system that uses a capsule type medical apparatus of the present embodiment. FIG. 2 is a block diagram showing an internal configuration of the capsule type medical apparatus in FIG. 1. FIG. 3 is a schematic sectional view showing an arrangement state of receiving electrodes included in the capsule type medical apparatus in FIG. 1. FIG. 4 is a block diagram showing an internal configuration of a communication device in FIG. 1. FIG. 5 is a schematic view showing a state where a signal is transmitted via a conductor existing in a subject.

As shown in FIG. 1, a capsule type medical system 101 includes, as essential parts, a capsule type medical apparatus 2 that is swallowed by a subject 1 and placed in a body cavity, and picks up an image of an object existing in the body cavity, a communication device 3 that is placed outside the subject 1 and can communicate with the capsule type medical apparatus 2, a terminal device 4 that performs processing based on a signal or the like received by the communication device 3, and displays the image of the object, and a portable storage medium 5 that can input, output and record data or the like accumulated in the communication device 3 and the terminal device 4.

To the communication device 3, one or more receiving antennas 6 that can receive a radio signal outputted from the capsule type medical apparatus 2, and transmitting electrodes 7a and 7b that are placed on a body surface of the subject 1, and can transmit various signals to the capsule type medical apparatus 2 placed in the body cavity are connected.

As shown in FIG. 2, the capsule type medical apparatus 2 includes, in a casing 10, a light emitting element 21 that is formed of for example, an LED and emits an illumination light for illuminating the object, a light emitting element drive circuit 22 that controls a driving state of the light emitting element 21, and an image pickup device 23 that is formed of, for example, a CCD (charge coupled device) or the like, picks up an image of the object illuminated by the light emitting element 21, and outputs the image of the object as an image pickup signal.

Further, the capsule type medical apparatus 2 includes, in the casing 10, receiving electrodes 30a and 30b, an inductor circuit 31a connected to the receiving electrode 30a and a GND potential, an inductor circuit 31b connected to the receiving electrode 30b and the GND potential, a signal receiving circuit 32, and a control circuit 33 that controls the light emitting element drive circuit 22, an image pickup device drive circuit 24, an image pickup signal processing circuit 25, and a modulation circuit 26 based on signals from the signal receiving circuit 32.

The receiving electrodes 30a and 30b are formed of for example, conductors (metal) such as aluminum or copper, and have configurations (described later) that can receive various signals transmitted from the transmitting electrodes 7a and 7b.

The inductor circuits 31a and 31b are configured to have the same inductance value (for example, 10 μH) as each other.

The signal receiving circuit 32 has a configuration that can perform processes such as amplification, demodulation and A/D conversion of the signal received by the receiving electrodes 30a and 30b and output the signal. The signal receiving circuit 32 also generates control signal receiving level data based on a signal level of the signal received by the receiving electrodes 30a and 30b, and outputs the data to the control circuit 33.

The signal level of the signal received by the receiving electrodes 30a and 30b is inputted to the signal receiving circuit 32 as a potential difference between two potentials: a potential generated between the receiving electrode 30a and the inductor circuit 31a, and a potential generated between the receiving electrode 30b and the inductor circuit 31b.

The control circuit 33 performs control on the modulation circuit 26 to superimpose the control signal receiving level data from the signal receiving circuit 32 on an image pickup signal transmitted from the image pickup signal processing circuit 25 to the modulation circuit 26. Thus, a radio signal with the control signal receiving level data superimposed on the image pickup signal is generated by the modulation circuit 26, and the radio signal is transmitted via a transmitting antenna 27 to the receiving antenna 6.

As shown in FIG. 3, the casing 10 includes a tip cover 10a formed into a substantially semi-spherical dome shape and a barrel cover 10b watertightly joined to each other, and is formed generally into a capsule shape. In the present embodiment, the casing 10 has a thickness of 0.5 mm and a maximum inner diameter of 10 mm of an inner portion of the capsule shape, and at least the barrel cover 10b is made of a material having a relative permittivity of about 4.

The tip cover 10a is made of a material having a high resistivity and a predetermined relative permittivity, having sufficient mechanical strength, and being transparent in an image pickup wavelength range, for example, cycloolefin polymer, polymer carbon, or the like and is formed into a substantially semi-spherical dome shape. The tip cover 10a has such a configuration, and thus the illumination light emitted from the light emitting element 21 passes to an outside of the casing 10, and a reflective light from the object illuminated by the illumination light passes to an inside of the casing 10.

The barrel cover 10b is made of, for example, polysulfone resin that is a dielectric material having a high resistivity and a predetermined relative permittivity (about 4), and has sufficient mechanical strength. The barrel cover 10b also has a capacity that can cover the components such as the above-described circuits.

As (schematically) shown in FIG. 3, the receiving electrodes 30a and 30b are formed to have the same shape (strip shape or tubular shape) as each other, and provided in tight contact with an inner wall side surface of the barrel cover 10b.

A demodulation circuit 41 demodulates the radio signal received by the receiving antenna 6 into an image pickup signal and outputs the signal.

A receiving signal processing circuit 42 performs processes such as A/D conversion or noise removal of the image pickup signal from the demodulation circuit 41 to generate image data, and outputs the generated image data to a memory circuit 46.

The receiving signal processing circuit 42 separates the control signal receiving level data superimposed on the image pickup signal and outputs the data to a control circuit 45 at timing before the above-described processes are performed.

A position detecting circuit 43 roughly detects a position where the capsule type medical apparatus 2 is located in a body of the subject 1 based on a signal level of the image pickup signal inputted to the demodulation circuit 41.

A user I/F 44 has a configuration that can perform various operation instructions by a user, and suggestion of various information to the user.

The control circuit 45 performs various controls of the components of the communication device 3 based on the operation instruction provided by the user I/F 44.

The control circuit 45 generates capsule control data for controlling the components of the capsule type medical apparatus 2 and outputs the data to a signal transmitting circuit 47 based on the operation instruction or the like provided by the user I/F 44.

The control circuit 45 performs control on the signal transmitting circuit 47 to generate an appropriate potential difference according to the control signal receiving level data between the transmitting electrode 7a and the transmitting electrode 7b based on the control signal receiving level data outputted from the receiving signal processing circuit 42.

The control circuit 45 analyzes the image of the object according to the image data based on the image data generated by the receiving signal processing circuit 42 and a detection result by the position detecting circuit 43. The control circuit 45 generates the position data indicating the position of the capsule type medical apparatus 2 in the body of the subject 1 based on the analysis result of the image of the object, and performs control on the memory circuit 46 to store the position data associated with the image data generated by the receiving signal processing circuit 42.

The memory circuit 46 is configured to be connectable to the portable storage medium 5. The memory circuit 46 successively stores the image data from the receiving signal processing circuit 42 and the position data associated with the image data based on the control by the control circuit 45.

With the above-described configuration, for example, when the portable storage medium 5 is connected to the memory circuit 46 and the user I/F 44 performs a predetermined operation, the control circuit 45 performs control according to the predetermined operation, and the image data accumulated in the memory circuit 46 and the position data associated with the image data are written in the portable storage medium 5.

The signal transmitting circuit 47 modulates the capsule control data from the control circuit 45, and thus generates a control signal as an external signal, and sets an amplitude level of a voltage of the control signal based on the control by the control circuit 45. The signal transmitting circuit 47 generates a potential difference according to the amplitude level of the voltage between the transmitting electrode 7a and the transmitting electrode 7b, and thus operates to pass a current according to the control signal through the body of the subject 1.

As shown in FIG. 4, the communication device 3 includes a battery 48 constituted by a power supply such as a primary battery or a secondary battery, and a power supply circuit 49 that generates a power supply voltage for operating the components of the communication device 3 based on electric power accumulated in the battery 48.

Now, an operation of the capsule type medical system 101 of the present embodiment will be described.

First, an operator or the like starts the components of the capsule type medical system 101, connects the receiving antenna 6, the transmitting electrode 7a, and the transmitting electrode 7b to the communication device 3, and places the transmitting electrode 7a and the transmitting electrode 7b on a body surface of the subject 1. Meanwhile, the capsule type medical apparatus 2 is swallowed by the subject 1 and placed in the body cavity of the subject 1.

The components of the capsule type medical apparatus 2 placed in the body cavity of the subject 1 operate with the frequency of image pickup, an exposure time, emission strength of the illumination light, and a signal processing parameter according to the control by the control circuit 33, illuminate the object, pick up an image of the object, and perform signal processing of an image pickup signal based on the image of the object.

The modulation circuit 26 generates a radio signal with the control signal receiving level data from the signal receiving circuit 32 superimposed on the image pickup signal from the image pickup signal processing circuit 25 and outputs the signal to the transmitting antenna 27 based on the control by the control circuit 33.

The radio signal transmitted from the transmitting antenna 27 is transmitted through the body of the subject 1 while being attenuated, and then received by the receiving antenna 6.

The demodulation circuit 41 of the communication device 3 demodulates the radio signal received by the receiving antenna 6 into an image pickup signal and outputs the signal.

The receiving signal processing circuit 42 performs processes such as A/D conversion or noise removal of the image pickup signal from the demodulation circuit 41 to generate image data, and outputs the generated image data to a memory circuit 46.

The receiving signal processing circuit 42 separates the control signal receiving level data superimposed on the image pickup signal and outputs the data to the control circuit 45 at timing before the above-described processes are performed.

The position detecting circuit 43 roughly detects the position where the capsule type medical apparatus 2 is located in the body of the subject 1 based on the signal level of the image pickup signal inputted to the demodulation circuit 41.

The control circuit 45 analyzes the image of the object according to the image data based on the image data generated by the receiving signal processing circuit 42 and the detection result by the position detecting circuit 43. The control circuit 45 generates the position data indicating the position of the capsule type medical apparatus 2 in the body of the subject 1 based on the analysis result of the image of the object, and the memory circuit 46 to store the position data associated with the image data generated by the receiving signal processing circuit 42.

The memory circuit 46 stores the image data from the receiving signal processing circuit 42 and the position data from the control circuit 45.

Meanwhile, when the control circuit 45 determines that the operation of the capsule type medical apparatus 2 or the control of the parameter or the like is required based on the image data generated by the receiving signal processing circuit 42, the position data generated by the control circuit 45, and the operation instruction provided by the user I/F 44, the control circuit 45 generates capsule control data according to the control and outputs the data to the signal transmitting circuit 47.

Factors that the control circuit 45 determines that the operation of the capsule type medical apparatus 2 or the control of the parameter or the like is required includes, for example, a case where various values are inputted by the user I/F 44 or a case where an object changes with progress of the capsule type medical apparatus 2. The capsule type medical apparatus 2 of the present embodiment has a configuration and an operation that can increase or reduce the frequency of image pickup for each change of the object with progress of the capsule type medical apparatus 2, and thus can perform control, for example, to prevent an image of an object where observation is unnecessary from being obtained, and intensively obtain an image of an object where the observation is necessary.

The control circuit 45 performs control on the signal transmitting circuit 47 to generate an appropriate potential difference according to the control signal receiving level data between the transmitting electrode 7a and the transmitting electrode 7b based on the control signal receiving level data outputted from the receiving signal processing circuit 42.

The signal transmitting circuit 47 modulates the capsule control data from the control circuit 45, and thus generates a control signal having a predetermined frequency (for example, 15 MHz), and sets an amplitude level of a voltage of the control signal based on the control by the control circuit 45. The signal transmitting circuit 47 generates a potential difference according to the amplitude level of the voltage between the transmitting electrode 7a and the transmitting electrode 7b, and thus operates to pass a current according to the control signal through an intra-body conductive substance 1a as a conductor existing in the subject 1.

The control circuit 45 does not control the signal transmitting circuit 47 based on the control signal receiving level data immediately after the components of the capsule type medical system 101 are started. Thus, the signal transmitting circuit 47 sets the amplitude level of the voltage of the control signal to a predetermined reference level (for example, 5 V/p-p) immediately after the components of the capsule type medical system 101 are started.

The current generated by the potential difference between the transmitting electrode 7a and the transmitting electrode 7b passes through the surface and the intra-body conductive substance 1a of the subject 1 and reaches an outer wall side surface of the barrel cover 10b, for example, as indicated by a bold arrow in FIG. 5.

The outer wall side surface of the casing 10 of the capsule type medical apparatus 2 comes into contact with a liquid such as a body fluid or a body wall wet with the liquid in the body cavity of the subject 1. In such a case, the barrel cover 10b having a property as a dielectric is held between the liquid such as a body fluid or the body wall wet with the liquid with an operation as a conductor, and the receiving electrodes 30a and 30b with an operation as a conductor. Thus, regions R1 and R2 including the intra-body conductive substance 1a, the barrel cover 10b, and the receiving electrodes 30a and 30b, surrounded by dotted lines in FIG. 5, can be regarded to each have a function equal to that of a capacitor element.

Specifically, the receiving electrodes 30a and 30b of the capsule type medical apparatus 2 can be regarded to each have a function equal to that of one side electrode of the capacitor element.

As shown in FIG. 5, the receiving electrode 30a is connected in series to the inductor circuit 31a. An inductance value (for example, 10 µH) of the inductor circuit 31a is set so that a portion including the region R1 and the inductor circuit 31a is configured as a resonant circuit having a frequency substantially equal to the predetermined frequency (for example, 15 MHz) of the control signal as a resonant frequency. Specifically, the portion including the region R1 and the inductor circuit 31a can be regarded to have a function substantially equal to that of an LC series resonant circuit (or LC high pass filter) having a predetermined resonant frequency (for example, 15 MHz).

As shown in FIG. 5, the receiving electrode 30b is connected in series to the inductor circuit 31b. An inductance value (for example, 10 µH) of the inductor circuit 31b is set so that a portion including the region R2 and the inductor circuit 31b is configured as a resonant circuit having a frequency substantially equal to the predetermined frequency (for example, 15 MHz) of the control signal as a resonant frequency. Specifically, the portion including the region R2 and the inductor circuit 31b can be regarded to have a function substantially equal to that of an LC series resonant circuit (or LC high pass filter) having a predetermined resonant frequency (for example, 15 MHz).

The frequency of the current (control signal) generated by the potential difference between the transmitting electrode 7a and the transmitting electrode 7b is substantially equal to the predetermined resonant frequency of the LC series resonant circuit including the region R1 and the inductor circuit 31a, and thus a voltage according to the current having reached the outer wall side surface of the barrel cover 10b is generated in the receiving electrode 30a.

Also, the frequency of the current (control signal) generated by the potential difference between the transmitting electrode 7a and the transmitting electrode 7b is substantially equal to the predetermined resonant frequency of the LC series resonant circuit including the region R2 and the inductor circuit 31b, and thus a voltage according to the current having reached the outer wall side surface of the barrel cover 10b is generated in the receiving electrode 30b.

Further, the intra-body conductive substance 1a has a resistance component, and thus a voltage drop occurs between the receiving electrode 30a and the receiving electrode 30b according to a distance between the two electrodes. Thus, a potential difference is generated between the receiving electrode 30a and the receiving electrode 30b.

The signal receiving circuit 32 generates control signal receiving level data based on the potential difference generated between the receiving electrode 30a and the receiving electrode 30b and outputs the data to the control circuit 33.

Further, the signal receiving circuit 32 amplifies the inputted potential difference, demodulates the control signal based on the amplified potential difference, performs A/D conversion of the control signal, and thus obtains capsule control data. The signal receiving circuit 32 outputs the obtained capsule control data to the control circuit 33.

The control circuit 33 performs control to change, for example, the frequency of image pickup per second, an exposure time, emission strength of the illumination light, and a signal processing parameter, or the like based on the capsule control data from the signal receiving circuit 32.

Meanwhile, the control signal receiving level data generated by the signal receiving circuit 32 is fed back to the communication device 3 through the above-described path. In the capsule type medical system 101 according to the present embodiment, such feedback is repeatedly performed, and thus the potential difference between the transmitting electrode 7a and the transmitting electrode 7b can be changed and set to a difference according to the control signal receiving level data. Thus, in the capsule type medical system 101 according to the present embodiment, the control signal transmitted from the communication device 3 and then transmitted via the intra-body conductive substance 1a can be stably received by the capsule type medical apparatus 2.

As described above, the receiving electrodes 30a and 30b as part of a receiving system in the capsule type medical apparatus 2 of the present embodiment do not have complicated configurations, and are provided in tight contact with the inner wall side surface of the barrel cover 10b and formed as strip-shaped or tubular metal. Only the inductor circuits are connected to the receiving electrodes 30a and 30b, which do not have complicated configurations. Further, as described above, it is sufficient that the signal receiving circuit 32 as apart of the receiving system in the capsule type medical apparatus 2 of the present embodiment has a circuit configuration that can amplify and demodulate a signal having a relatively low frequency (for example, 15 MHz) and transmitted via the intra-body conductive substance 1a.

Thus, the capsule type medical apparatus 2 in the capsule type medical system 101 according to the present embodiment can be easily configured and can receive an external signal from an outside of the body by the receiving system with a reduced circuit scale as compared with a conventional receiving system having a configuration for receiving an external signal (radio signal) having a relatively high frequency. Also, the capsule type medical apparatus 2 in the capsule type medical system 101 according to the present embodiment can receive an external signal from an outside of the body by a receiving system with lower power consumption in operation as compared with the conventional receiving system having a configuration for receiving an external signal (radio signal) having a relatively high frequency.

Generally, as a medical observation apparatus, an endoscope apparatus is known that picks up an image of an inside of a body cavity of a subject such as a patient, and displays the image on a monitor. A general endoscope apparatus includes a flexible distal end portion and is inserted through the mouth, and an image pickup portion provided on a distal end portion side or aproximal end portion side picks up an image of a lesion or the like to be observed.

As an endoscope apparatus having a different configuration as the above-described endoscope apparatus, a capsule type endoscope apparatus has a configuration in which a capsule type endoscope body including an image pickup device and lighting equipment sealed in a capsule type exterior portion. The capsule type endoscope apparatus is swallowed by the patient through the mouth, picks up images many times while passing through an inside of a body cavity, and transmits image pickup data thereof. The image pickup data is received by a receiving portion of a capsule type endoscope system, and displayed on a screen of a display portion. For example, a swallowing-type capsule type endoscope system described in Japanese Patent Application Laid-Open Publication No. 2006-513670 has an image pickup function and a communication function using a living body (hereinafter referred to as living body communication). After the endoscope system is swallowed through the mouth for observation of an inside of a subject and before naturally discharged to an outside of a body cavity, the endoscope system passes through an inside of the body cavity, for example, an inside of organs such as stomach or small intestine with peristaltic movement thereof and successively picks up images. While the endoscope system passing through the inside of the body cavity, image data picked up by the capsule type endoscope apparatus is transmitted to an outside by the living body communication and stored in a memory provided in the outside in each case.

However, the technique described in Japanese Patent Application Laid-Open Publication No. 2006-513670 is a system in which two transmitting electrodes exposed on an exterior of the capsule type endoscope apparatus both come into contact with a body wall in a gastrointestinal tract and performs communication. The capsule type endoscope apparatus that moves in the body cavity moves on many rugae on a gastrointestinal tract surface with peristaltic movement, and thus is placed in various orientations in the gastrointestinal tract. If the two electrodes do not come into contact with the body wall in the gastrointestinal tract at shooting timing (at data transmission), proper communication is not performed and image data cannot be obtained. In view of such circumstances, the proposed communication system using the living body with the two transmitting electrodes is not necessarily optimal.

Thus, for example, with a configuration as described below, a system is provided that has a communication function using a living body, enlarges a conductive region between an electrode used for communication and a body wall when the capsule type endoscope apparatus moves in a body cavity with peristaltic movement, and thus maintains a proper electric contact state and allows stable communication irrespective of the orientation.

Figure 6:
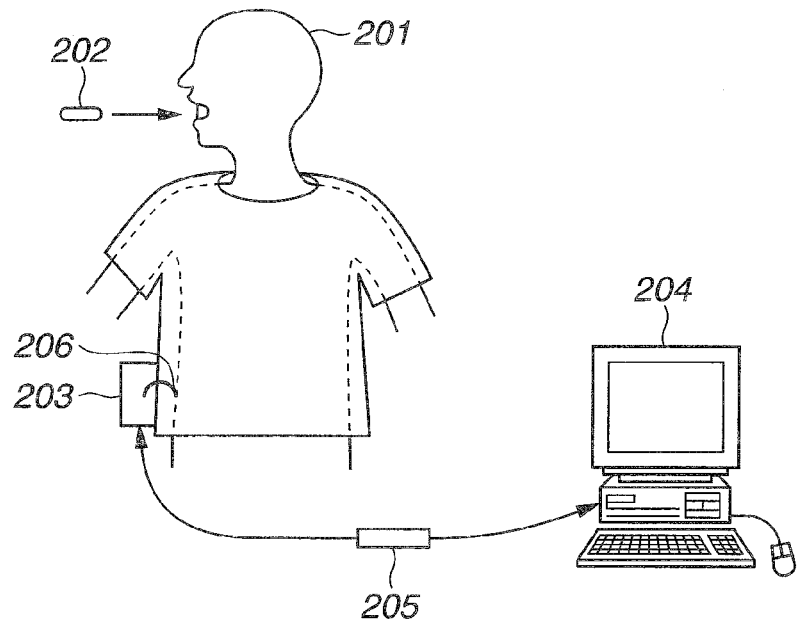
FIG. 6 is a view showing an example of a configuration of an intra-subject information obtaining system using a capsule type endoscope apparatus.

FIG. 6 is a view showing an example of a configuration of an intra-subject information obtaining system. The intra-subject information obtaining system described below is, specifically, a system that uses a capsule type endoscope apparatus that holds water in a communication transmission line of communication using a living body (hereinafter referred to as living body communication), and performs communication via the water.

First, a water holding method of the capsule type endoscope apparatus will be described. Water is held between a capsule type endoscope and an exterior cover portion having a plurality of holes, and to prevent the water once held between the capsule type endoscope and the exterior cover portion from flowing out of the exterior cover portion, surface tension of the water needs to be higher than an external force applied to the water. This is expressed by an inequality:

mg (force applied to water)<$2\pi r\gamma$(force to stop water)

m: mass of water g: acceleration of gravity r: radius of exterior cover hole $\gamma$: surface tension When "left-hand side=right-hand side" is satisfied at this time, water flows out of the exterior cover portion.

mg (force applied to water)=$\pi r^2 h\rho g$<$2\pi r\gamma$(force to stop water)

where $\rho$ is density of water, and h is height of water.

Both sides are rearranged:

rh$\rho$g (force applied to water)<$2\gamma$(force to stop water)

From this inequality, water does not flow out of the exterior cover portion with smaller r and h.

Now, the intra-subject information obtaining system will be described.

As shown in FIG. 6, the capsule type endoscope system includes a capsule type endoscope apparatus 202 that is administered through the mouth of a subject 201, passes through an inside of a body cavity, and collects intra-body information of the subject 201, a communication device 203 that is a device outside a body that is placed near the outside of the body of the subject 201 and communicates various information with the capsule type endoscope apparatus 202, and a data transmitting and receiving portion 206 for transmitting and receiving data. The capsule type endoscope system includes a display device 204 that displays an image based on data received by the communication device 203, and a portable recording medium 5 that inputs and outputs data between the communication device 203 and the display device 204. The data transmitting and receiving portion 206 includes one or more electrodes.

Next, the capsule type endoscope apparatus 202 will be described.

Figure 7A:
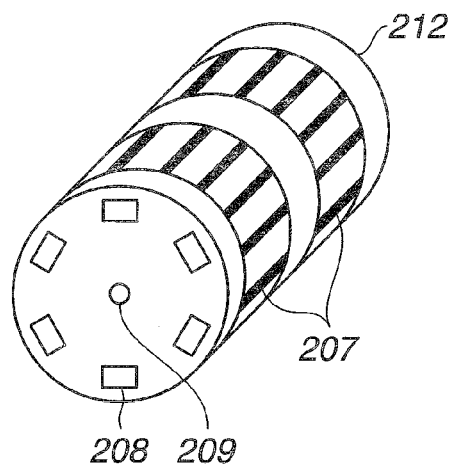
FIG. 7A is a perspective view showing an appearance configuration of the intra-subject information obtaining system.
Figure 7B:
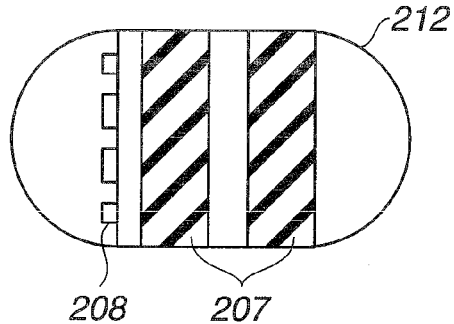
FIG. 7B is a side view showing the appearance configuration of the intra-subject information obtaining system.
Figure 13:
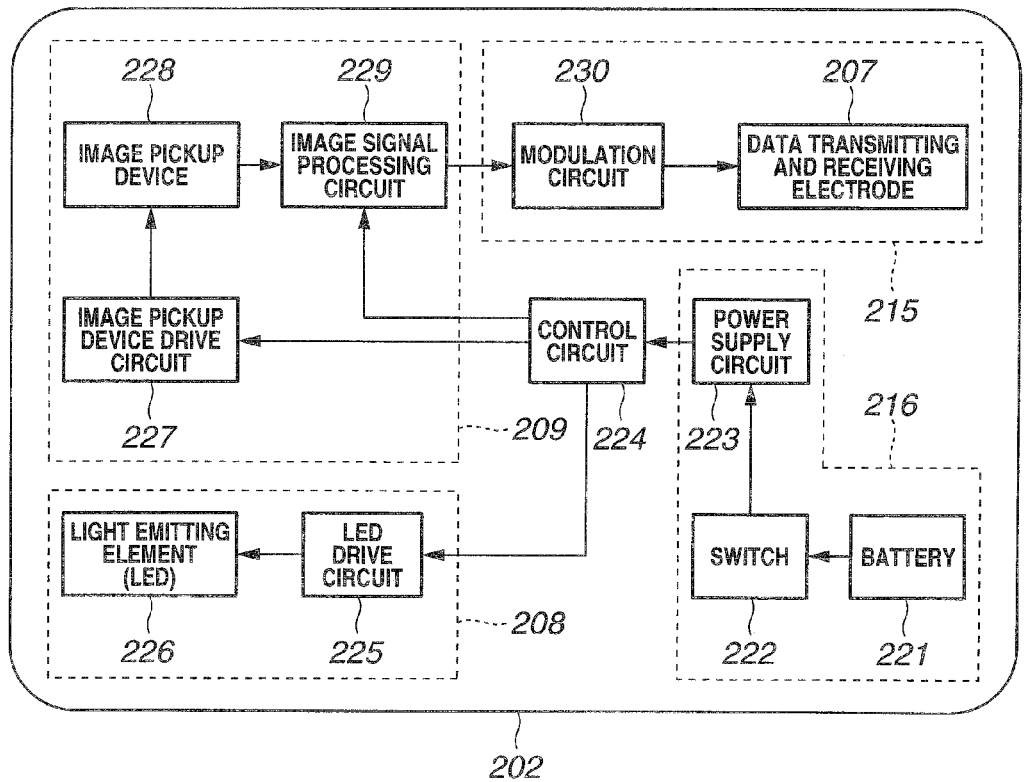
FIG. 13 is a view showing an example of a configuration of the capsule type endoscope apparatus.
Figure 14:
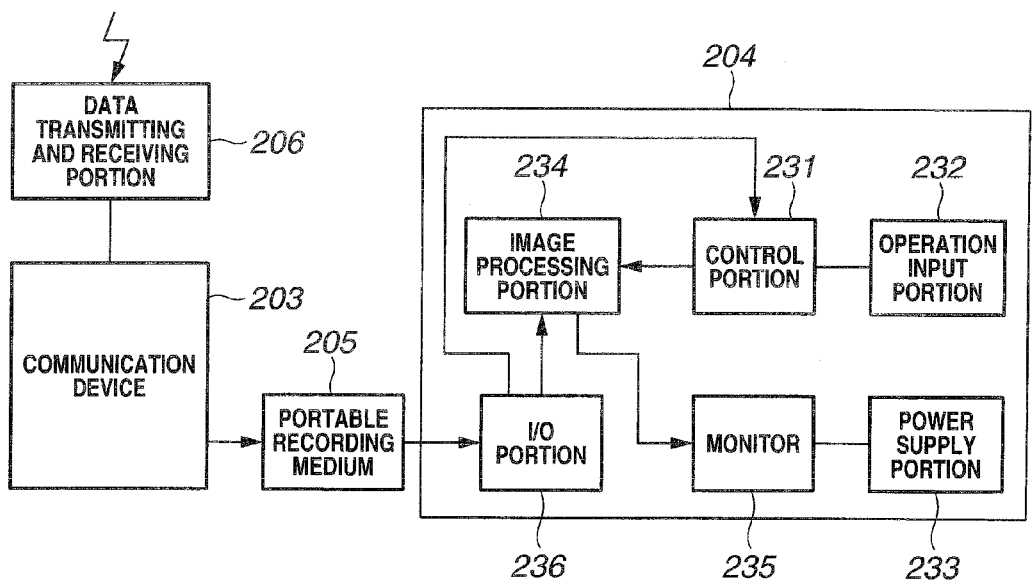
FIG. 14 is a view showing an example of configurations of a data transmitting and receiving portion, a communication device, and a display device.

FIGS. 7A and 7B are views showing an appearance configuration of the capsule type endoscope apparatus 202. FIG. 13 is a view showing an example of a configuration of the capsule type endoscope apparatus 202. FIG. 14 is a view showing an example of configurations of the data transmitting and receiving portion 206, the communication device 203, and the display device 204.

The capsule type endoscope apparatus 202 shown in FIGS. 7A and 7B includes an image pickup portion 209, a lighting portion 208 that illuminates an image pickup range (angle of view) thereof to required brightness, a control portion (control circuit 224 in FIG. 13) described later that controls driving of the image pickup portion 209 and the lighting portion 208, a power supply portion (power supply portion 216 in FIG. 13) described later, and a communication portion (communication portion 215 in FIG. 13) described later having a data transmitting and receiving electrode 207. The above-described portions are housed in an exterior portion 212 of a cylindrical shape with semispherical bodies on a front and a rear, a so-called capsule shape.

The exterior portion 212 of the capsule type endoscope apparatus 202 is harmless to a living body or a human body as the subject 201, and made of an insulating material. The exterior portion 212 includes two-divided front and rear portions, which are fitted to each other and fixedly bonded after an endoscope apparatus body is housed therein. The endoscope apparatus body may be sealed with integrally molded resin. At this time, at least an image pickup range of an image pickup device is transparent resin. The exterior portion 212 includes a transparent exterior portion that covers an image pickup surface side of the image pickup portion 209, and a colored exterior portion on a rear of the image pickup portion 209.

Two data transmitting and receiving electrodes 207 that perform communication by living body communication are formed on and wound around an outer peripheral surface of the exterior portion 212 into a ring shape. The data transmitting and receiving electrode 207 is made of a conductive substance having high resistance to corrosion and harmless to a human body on as to withstand a reactive substance such as digestive juice in the subject 201. Specifically, the data transmitting and receiving electrode 207 is made of, for example, stainless SUS316L, titanium, or gold. FIGS. 7A and 7B show a configuration with the two electrodes, but not limited to this, a configuration with a single electrode or multiple electrodes may be allowed.

The configuration of the capsule type endoscope apparatus 202 shown in FIG. 13 will be described.

The above-described control portion includes a control circuit 224 including a processing arithmetic operation element such as a CPU and a storage element that stores a predetermined application, and controls the components in the capsule type endoscope apparatus 202. The image pickup portion 209 includes an image pickup device 228 that performs photoelectric conversion of an optical image formed via a transparent exterior member described later and generates a gastrointestinal tract image signal, an image pickup device drive circuit 227 that drives the image pickup device 228 (image capturing operation), and an image signal processing circuit 229 that performs general image processing of the gastrointestinal tract image signal obtained from the image pickup device 228 and generates image data.

The communication portion 215 includes a modulation circuit 230 that modulates image data into a communication signal, and a data transmitting and receiving electrode 207 that transmits a communication signal including image data and information on the image data to the data transmitting and receiving portion 206. As the image pickup device 228, for example, a charge coupled device (CCD) image sensor or a CMOS image sensor is used. A configuration may be allowed that generates a three-dimensional image using pupil dividing by a plurality of image pickup devices each having an image forming optical system, or one image pickup device and a plurality of image forming optical systems.

The lighting portion 208 includes a light emitting element (LED) 226 that emits a light of high brilliance, and an LED drive circuit 225 that drives the light emitting element 226 to emit a light according to light emitting timing or light emitting brilliance by an instruction from the control circuit 224. The light emitting element 226 intermittently emits a light in synchronization with image pickup timing, and uses a light of wavelength that facilitates finding a diseased part. The intermittent light emission by the light emitting element 226 can prevent a temperature increase by the lighting portion and reduce power consumption. Also, a plurality of light emitting elements 226 may be used and arranged around the image pickup device in a dispersed manner.

The power supply portion includes, for example, a battery 221 constituted by a small battery, a power supply circuit 223 that converts power supplied from the battery 221 into a driving voltage, and a switch 222 that is provided between the battery 221 and the power supply circuit 223 and turned on by an external operation. When the switch 222 is turned on, the power is inputted from the battery 221 to the power supply circuit 223, and supply of the driving voltage to the components is started.

FIG. 14 is a view showing an example of configurations of the data transmitting and receiving portion 206, the communication device 203, and the display device 204.

The data transmitting and receiving portion 206 receives a communication signal transmitted by communication using a living body of the subject 201 from the data transmitting and receiving electrode 207, and propagates the signal to the communication device 203 connected by a cable. The communication device 203 performs processes such as demodulation or the like of the received communication signal, and reproduces the signal as a gastrointestinal tract image signal.

At this time, when the image signal processing circuit 229 in the capsule type endoscope apparatus 202 does not perform digitalization of the image signal, the communication device 203 performs image processing of the reproduced gastrointestinal tract image signal, and then the signal is stored as image data in a removable portable recording medium 205 such as a USB memory.

The display device 204 includes an input/output portion (I/O portion) 236 that inputs and outputs an information signal including image data to and from the mounted portable recording medium 205, an image processing portion 234 that converts the signal to a video signal for displaying image data and corrects color or the like, a monitor 235 that displays the video signal on a screen, a power supply portion 233 that receives electric power from a battery or a commercial power supply and supplies power for driving to the components, a control portion 231 that controls the entire display device, and an operation input portion 232 constituted by a keyboard, a touch panel, or a mouse for inputting user's instructions or settings. The display device 204 may be constituted by a personal computer.

For the above-described configuration of the intra-subject information obtaining system, the example in which the gastrointestinal tract image is transmitted from the capsule type endoscope apparatus 202 to the data transmitting and receiving portion 206 has been described, but of course, data signal may be transmitted from the data transmitting and receiving portion 206 to the capsule type endoscope apparatus 202. In this case, it is sufficient that a circuit that converts a communication signal into an original instruction signal or a data signal, such as a demodulation circuit connected to the data transmitting and receiving electrode 207, is provided in the capsule type endoscope apparatus 202 shown in FIG. 13. The communicated signal is not limited to the signal by image data, but a trigger signal or the like may be transmitted.

Figure 8:
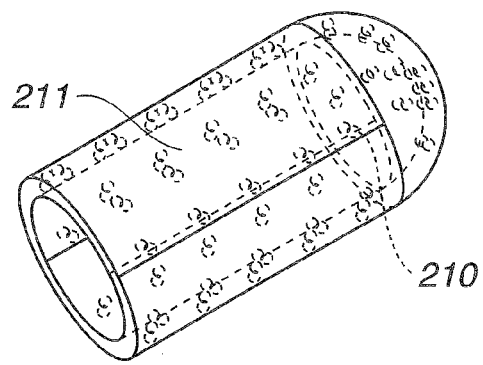
FIG. 8 is a view showing an appearance configuration of an exterior cover portion fitted over a capsule type endoscope apparatus.

Next, with reference to FIG. 8, the exterior cover portion 211 fitted over the capsule type endoscope apparatus 202 will be described.

The exterior cover portion 211 is made of an insulating material, for example, resin and has many holes 210 opened at substantially regular intervals covering entirely. The exterior cover portion 211 is made of an insulating substance having resistance to corrosion and harmless to a human body so as to withstand a reactive substance such as digestive juice in the subject 201 like the data transmitting and receiving electrode 207. A slight gap extends between an inner surface of the exterior cover portion 211 and an outer surface of the capsule type endoscope apparatus 202, and can hold water with such a configuration.

Figure 9A:
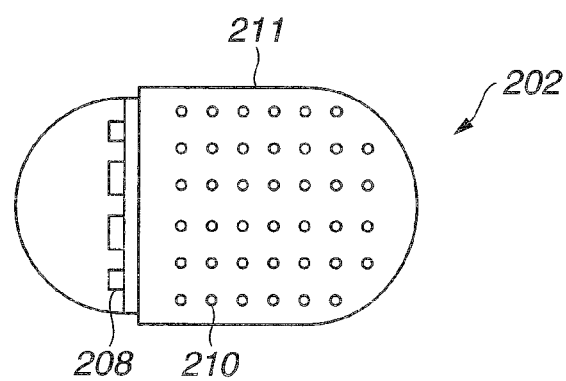
FIG. 9A is a side view showing a state where the exterior cover portion is fitted over the capsule type endoscope apparatus.
Figure 9B:
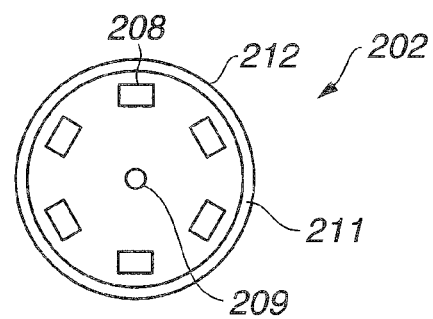
FIG. 9B is a front view showing a state where the exterior cover portion is fitted over the capsule type endoscope apparatus.

FIGS. 9A and 9B show a state where the exterior cover portion 211 is fitted over the capsule type endoscope apparatus 202. The exterior cover portion 211 covers a portion other than the image pickup portion, and the holes 210 face the data transmitting and receiving electrode 207.

Water having entered the holes 210 reaches the data transmitting and receiving electrode 207, and further spreads in the gap between the exterior cover portion 211 and the capsule type endoscope apparatus 202. Specifically, electrical connection is provided so that water in one hole 210 is just coupled to water on a body surface of the subject 201, and water spreads to the data transmitting and receiving electrode 207 via the water spreading in the gap.

Thus, the water exists in the hole 210 and in the gap between the capsule type endoscope apparatus 202 and the exterior cover portion 211, and comes into contact with at least a body wall surface of the subject 201, and a data transmission line from the data transmitting and receiving electrode 207 to the communication device 203 is reliably formed. Specifically, as a transmission line of the transmitted communication signal, the signal is transmitted from the data transmitting and receiving electrode 207 via the water and the subject 201 to the communication device 203, and further transmitted from the communication device 203 via the subject 201 and the water to the data transmitting and receiving electrode 207.

To provide the water holding state, the capsule type endoscope apparatus 202 may be placed in water to soak the gap with water before the capsule type endoscope apparatus 202 is swallowed by the subject 201. The water in this case is pure water, tap water, saline solution, or Ringer's solution. It is not always necessary to previously soak the gap with water, and when the capsule type endoscope apparatus 202 moves in the subject with peristaltic movement, sufficient water can be ensured in a stomach.

In the above-described configuration of the intra-subject information obtaining system, the exterior cover portion 211 having many holes opened is fitted over the capsule type endoscope apparatus 202, and thus a transmission line is formed via the water entering the hole 210 even if the subject 201 and the two data transmitting and receiving electrodes 207 do not come into direct contact with each other. Thus, the data transmitting and receiving electrodes 207 always holding water with respect to the body wall of the subject 201 moves in the subject 201, and even if the capsule type endoscope apparatus 202 is in an unstable orientation with respect to the body wall, electrical conduction can be provided to allow stable communication.

According to the above-described intra-subject information obtaining system, the system has the communication function using the living body, and the data transmitting and receiving electrode used for communication and the body wall of the subject maintains a proper electrical contact state via water when the capsule type endoscope apparatus moves in the body cavity with peristaltic movement, thereby allowing stable communication irrespective of the orientation.

Next, another exemplary configuration of an exterior cover portion of a capsule type endoscope apparatus 202 will be described.

In the exemplary configuration, water holding means using capillarity with fiber is used. The capillarity is a phenomenon in which a liquid is sucked and passes through a tubular object. Specifically, the capillarity is a phenomenon in which the liquid is moved by surface tension of an inner wall of the tubular object, wettability, and density of the liquid, and the liquid is moved until a force of movement becomes equal to an external force such as gravity. At this time, an increasing height h (m) of a liquid level is expressed by $h = 2T \cos \theta / \rho g r$, where T: surface tension (N/m), $\theta$: contact angle (°), p: density of liquid (kg/m$^3$), g: acceleration of gravity (m/sec$^2$), and r: inner radius of tube (m).

Figure 10A:
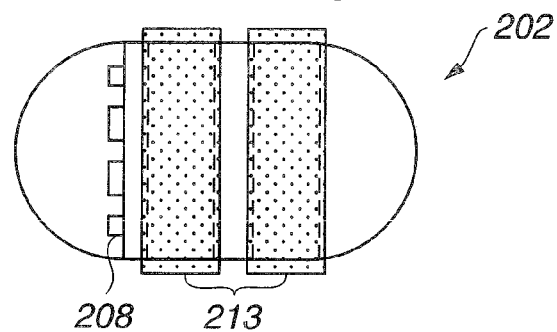
FIG. 10A is a view showing an example of an appearance configuration of the capsule type endoscope apparatus over which a fiber cover portion is fitted.
Figure 10B:
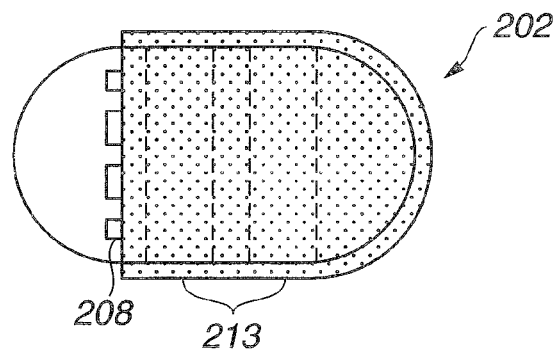
FIG. 10B is a view showing a different example from FIG. 10A of an appearance configuration of the capsule type endoscope apparatus over which a fiber cover portion is fitted.

FIGS. 10A and 10B show an example of a configuration of a case where a fiber cover portion 213 is used instead of the exterior cover portion 211 of the capsule type endoscope apparatus 202.

In the exemplary configuration, as shown in FIGS. 10A and 10B, the fiber cover portion 213 covering the data transmitting and receiving electrode 207 is provided. The fiber cover portion 213 is made of a material poorly soluble in a body fluid in the gastrointestinal tract, for example, chitin fiber, high-absorbent polymer, or the like, as woven fabric or non-woven fabric. Of course, the fiber cover portion 213 can absorb and hold water in the subject 201. The fiber cover portion 213 completely covers the data transmitting and receiving electrode 207, and is secured to the capsule type endoscope apparatus 202 by applying an adhesive or the like to a portion beyond the data transmitting and receiving electrode 207 (portion without abutment). The fiber cover portion 213 is placed to cover the portion other than the image pickup portion like the exterior cover portion 211, but not limited to this, the fiber cover portion 213 may be placed in any manners as long as it is placed to come into contact with the data transmitting and receiving electrode 207.

According to the exemplary configuration, the operation and effect equal to the exemplary configuration using the exterior cover portion 211 can be obtained. Further, according to the exemplary configuration, the woven fabric or non-woven fabric absorbs and holds water, and thus can hold more water than the exterior cover portion made of resin. Also, even if the water is released, the fiber cover portion 213 again comes into contact with the body wall in the subject and can again suck and hold water in the gastrointestinal tract.

Next, another exemplary configuration of an electrode provided in a capsule type endoscope apparatus 202 will be described.

Figure 11A:
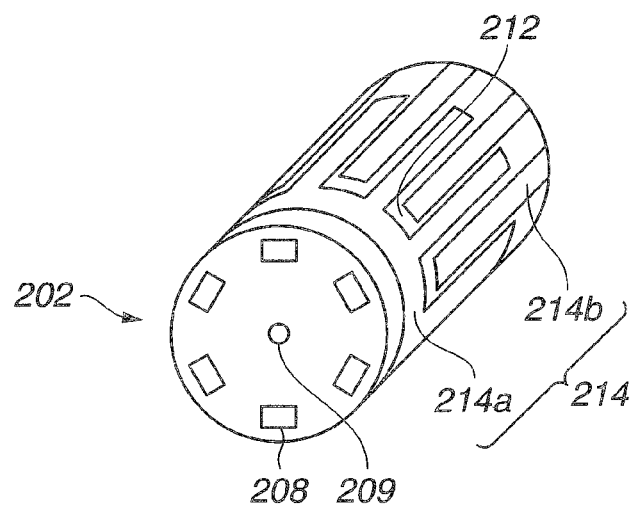
FIG. 11A is a perspective view showing an appearance configuration of a comb electrode.
Figure 11B:
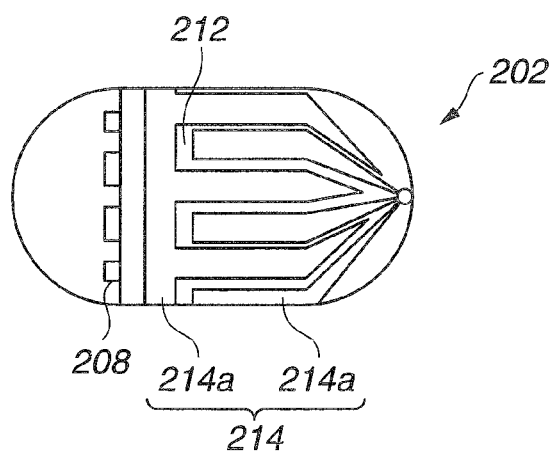
FIG. 11B is a side view showing the appearance configuration of the comb electrode.
Figure 12A:
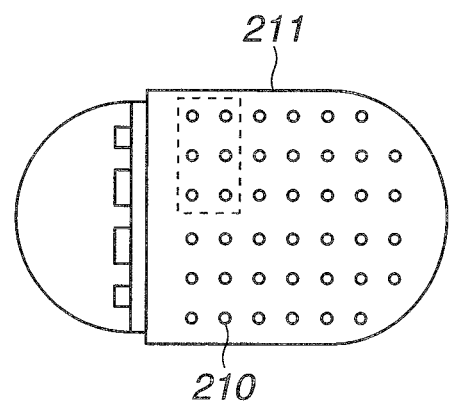
FIG. 12A is an outline view showing a positional relationship between a data transmitting and receiving electrode and a hole.
Figure 12B:
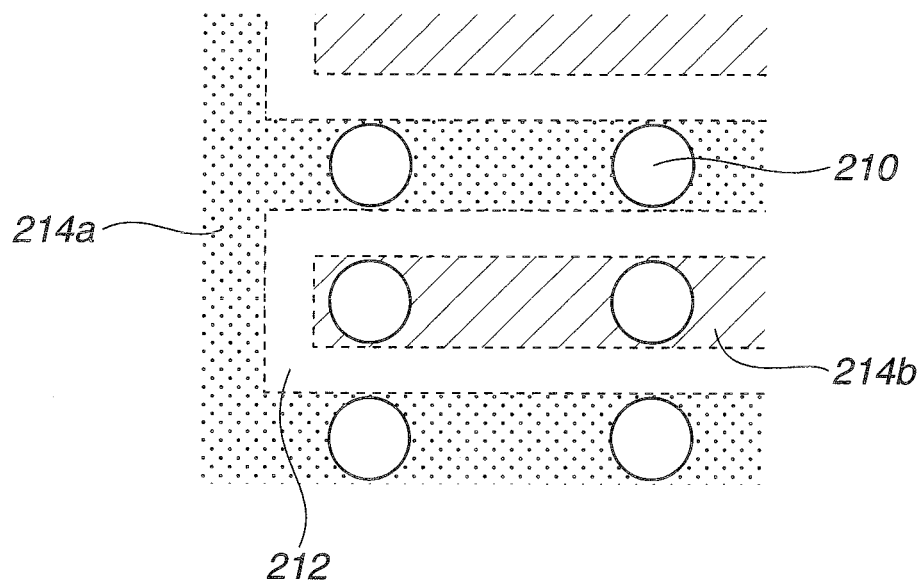
FIG. 12B is a detailed view showing the positional relationship between the data transmitting and receiving electrode and the hole.

As shown in FIGS. 11A, 11B, 12A and 12B, a capsule type endoscope apparatus 202 in the exemplary configuration uses a comb electrode as an electrode. FIGS. 11A and 11B are views showing an appearance configuration of the comb electrode. FIGS. 12A and 12B are views showing a positional relationship between the data transmitting and receiving electrode 207 and the hole 210.

As shown in FIGS. 11A and 11B, on a surface of an exterior portion 212 of the capsule type endoscope apparatus 202, comb-shaped data transmitting and receiving electrodes (hereinafter referred to as comb-shaped electrodes) 214a and 214b that mesh without contact are formed. The comb shape in the exemplary configuration indicates, for example, a state where electrodes are alternately placed from left and right like fingers of both hands opened and put together. Specifically, the comb-shaped electrodes 214a and 214b includes, as shown in FIG. 11B, the comb-shaped electrode 214a extending from a side of an lighting portion 208 on a front, and the comb-shaped electrode 214b extending forward from a rear end side. The electrodes alternately extend without contact to constitute the comb-shaped electrodes 214a and 214b. The comb-shaped electrode 214b converges to a rear end of the exterior portion 212.

Also, as shown in FIG. 12A, an exterior cover portion 211 having holes 210 opened covering entirely is fitted over the exterior portion 212 on which the data transmitting and receiving electrode 214 of the capsule type endoscope apparatus 202 is formed.

As shown in FIG. 12B, the holes 210 are opened in positions where the surface of the data transmitting and receiving electrode 207 is exposed.

When water in the subject 201 comes into contact with the exterior cover portion 211, the water comes into contact with the water held in each hole 210. Thus, like the configuration shown in FIG. 8, an electric transmission line from the data transmitting and receiving electrode 207 to the communication device 203 is formed, and a current of a communication signal flows from the data transmitting and receiving electrode 214a→water→subject 201→communication device 203→subject 201→water→data transmitting and receiving electrode 214b, and thus communication using a living body is performed.

However, in the configuration shown in FIGS. 11A, 11B, 12A and 12B, distances to the data transmitting and receiving electrodes 214a and 214b are short, and thus a high current value can be maintained to increase communication accuracy. Also, only a small amount of water is required for forming the transmission line. The exterior cover portion 211 in the present embodiment may be the above-described fiber cover portion 228.

Figure 15:
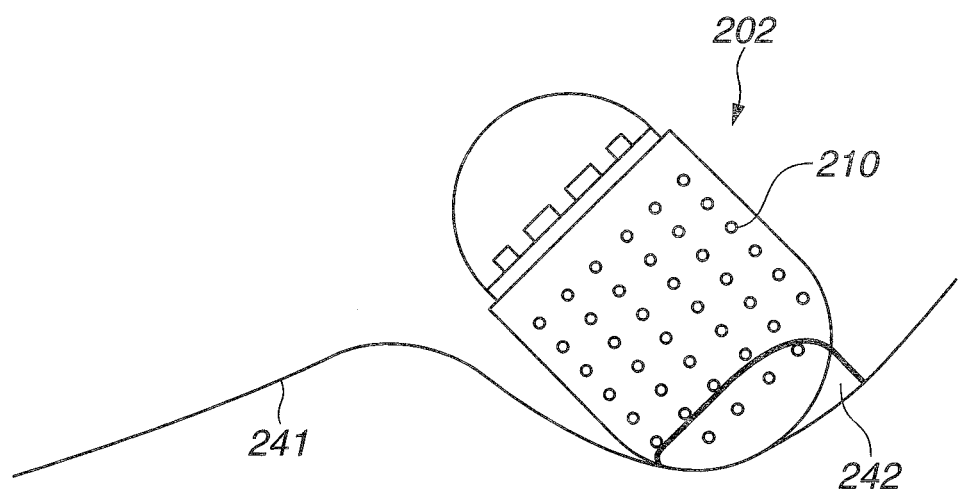
FIG. 15 is a view showing an orientation of the capsule type endoscope apparatus in the subject.

As such, the comb-shaped electrodes 214a and 214b are used, and thus as shown in FIG. 15 communication can be performed even if the capsule type endoscope apparatus 202 is in an orientation in the subject 1 such that the image pickup portion 209 is raised to be oriented upwardly and only a rear end comes into contact with water 242 on a body wall 241.

Next, with reference to FIGS. 13 and 14, driving of the capsule type endoscope apparatus 202 in the above-described exemplary configurations will be described. The exemplary configurations have different configurations or shapes of the data transmitting and receiving electrode 207 and the exterior cover portion 211, but have the same communication style of the gastrointestinal tract image.

The capsule type endoscope apparatus 202 is in an initial state before administered to the subject 201, and the battery 221 is separated from the power supply circuit 223 by the switch 222. When the switch 222 is turned on by an external operation, the battery 221 is electrically connected to the power supply circuit 223, and power is supplied to the components. Then, the control circuit 224 starts control, the image pickup portion 209 picks up an image under illumination of the lighting portion 208, and the gastrointestinal tract image of the subject 201 is obtained. Then, the gastrointestinal tract image is transmitted to the display device 204 by communication and displayed on the screen.

Specifically, the control circuit 224 performs control to drive the LED drive circuit 225, and the light emitting element 226 emits a light to irradiate an image pickup range with an illumination light, the image pickup device drive circuit 227 drives the image pickup device 228, and the gastrointestinal tract image of the subject 201 is obtained. The gastrointestinal tract image is converted into a gastrointestinal tract image signal by the image signal processing circuit 229. The gastrointestinal tract image signal is modulated by the modulation circuit 230, and transmitted from the data transmitting and receiving electrode 207 to the data transmitting and receiving portion 206 by communication using the living body (subject 201).

The gastrointestinal tract image signal transmitted to the data transmitting and receiving portion 206 is accumulated and stored, for example, in the portable recording medium 205 such as a USB memory stick. The portable recording medium 205 is connected to an I/O port (not shown) provided in the display device 204. Of course, without any connection with a limit to an activity range of the subject 201 (human subject), the communication device 203 and the display device 204 may be connected by a communication cable to transmit the gastrointestinal tract image signal.

In the display device 204, the gastrointestinal tract image signal read out from the portable recording medium 205 is inputted to an image processing portion 234 via an I/O portion 236. The image processing portion 234 performs signal processing such as demodulation of the gastrointestinal tract image signal, and displays the signal as a gastrointestinal tract image on a monitor 235. At this time, information on the gastrointestinal tract image is also displayed on the screen.

In the above-described exemplary configurations, the example in which the gastrointestinal tract image is transmitted from the capsule type endoscope apparatus 202 to the communication device 203 has been described, but not limited to the transmission of the image signal, a data signal may be transmitted from the communication device 203 to the capsule type endoscope apparatus 202.

As described above, according to the above-described configurations, in whichever orientation the capsule type endoscope apparatus 202 is placed in the subject, electrical conduction is provided between the data transmitting and receiving electrode and the body wall by water, and stable and reliable communication using a living body can be performed. Thus, gastrointestinal tract images can be continuously obtained from the subject without any dropout.

The present invention is not limited to the above-described embodiments, but it should be understood that various changes or applications may be made without departing from the gist of the invention.

What is claimed is:
1. A capsule type medical system comprising:
an external device that is provided outside a subject and can use a conductor existing in the subject as a transmission medium to transmit an external signal to an inside of the subject; and
a capsule type medical apparatus that can receive the external signal while moving in the subject,
wherein the capsule type medical apparatus includes:
a cover member that is formed of a dielectric and covers components of the capsule type medical apparatus;
a plurality of electrodes that are formed of conductors, are provided in tight contact with an inner wall side surface of the cover member, and receive the external signal;
an inductor circuit that is connected in series to each of the plurality of electrodes, and has an inductance value set to configure a resonant circuit having a fre- quency substantially equal to a carrier frequency of the external signal as a resonant frequency;

a signal receiving circuit to which the external signal received by the plurality of electrodes and a potential difference of the external signal are input, and which is configured to generate receiving level data according to a receiving level of the external signal, based on the inputted potential difference;

an image pickup portion that picks up an image of an inside of the subject and outputs an image pickup signal; and a signal transmitting portion that transmits the image pickup signal outputted from the image pickup portion and the receiving level data generated by the signal receiving circuit to an outside of the capsule type medical apparatus according to control based on the external signal, wherein the external device includes:

a position detecting section configured to roughly detect a position of the capsule type medical apparatus in the subject based on a signal level of the image pickup signal received from the signal transmitting portion; and a control section configured to generate position information by performing an analysis based on an image obtained by performing signal processing on the image pickup signal sent from the signal transmitting portion and the position of the capsule type medical apparatus roughly detected by the position detecting section, and further configured to perform control to store the generated position information to be associated with the image.

2. The capsule type medical system according to claim 1, wherein the inductance value of the inductor circuit that is connected in series to each of the plurality of electrodes is the same as each other.

3. The capsule type medical system according to claim 1, wherein the control section adjusts an output level of the external signal based on the receiving level data transmitted from the signal transmitting portion.

4. The capsule type medical system according to claim 1, wherein the cover member is made of a material having a relative permittivity of about 4, a casing including the cover member has a thickness of 0.5 mm and a maximum inner diameter of 10 mm, the plurality of electrodes have the same shape as each other, the inductance value is 10 pH, and the carrier frequency is 15 MHz.

5. The capsule type medical system according to claim 1, wherein the resonant frequency is 15 MHz.

* * * * *